United States Patent

Zajac

Patent Number: 5,824,293
Date of Patent: Oct. 20, 1998

[54] NAIL POLISHING METHOD AND PRODUCT

[76] Inventor: John Zajac, 1137 Angmar Ct., San Jose, Calif. 95121

[21] Appl. No.: 522,751

[22] Filed: Sep. 1, 1995

[51] Int. Cl.⁶ .............................. A61K 7/04; A61K 9/00
[52] U.S. Cl. ............................................. 424/61; 424/400
[58] Field of Search ...................... 132/73, 285; 424/61, 424/401; 427/154, 282

[56] References Cited

U.S. PATENT DOCUMENTS

| | | | |
|---|---|---|---|
| 5,165,962 | 11/1992 | Daly | 427/235 |
| 5,308,647 | 5/1994 | Lappi | 427/154 |
| 5,420,015 | 5/1995 | Wuerch | 106/162 |

*Primary Examiner*—Thurman K. Page
*Assistant Examiner*—Sharon Howard
*Attorney, Agent, or Firm*—Flehr Hohbach Test Albritton & Herbert LLP

[57] ABSTRACT

Nail polishing method and product in which a masking material is applied to the skin or tissue surrounding a nail, and any portions of the material on the nail are removed to form a sharp line of demarcation between the nail and the surrounding skin or tissue. A nail polishing lacquer is applied to the nail and to portions of the masking material adjacent to the nail, After the lacquer has dried, a solvent is rubbed onto the masking material to break off and dissolve the material and thereby remove that material and any lacquer on it from the skin or tissue around the nail. In one disclosed embodiment, the masking material comprises a mixture of liquid detergent, toothpaste, a coloring agent, and water.

13 Claims, 1 Drawing Sheet

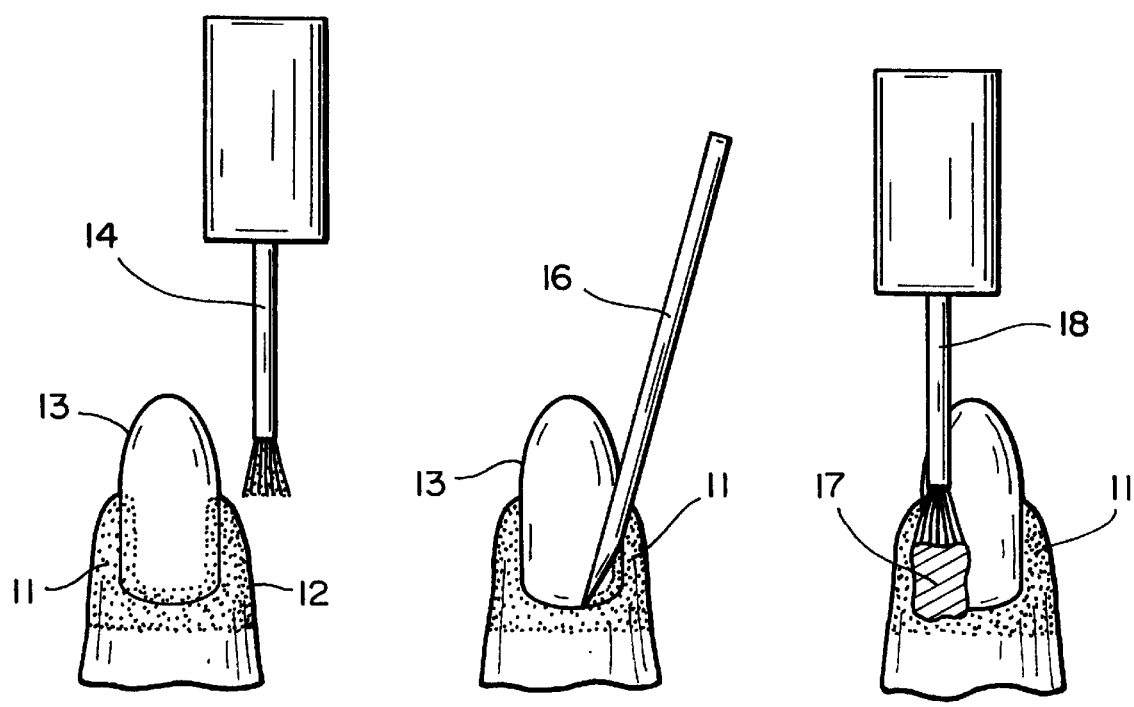
FIG_1  FIG_2  FIG_3
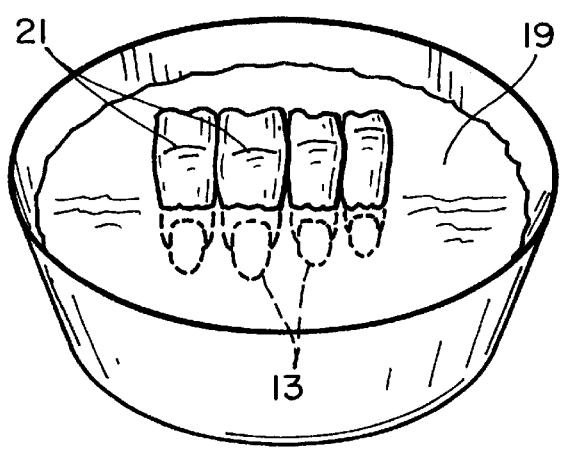
FIG_4
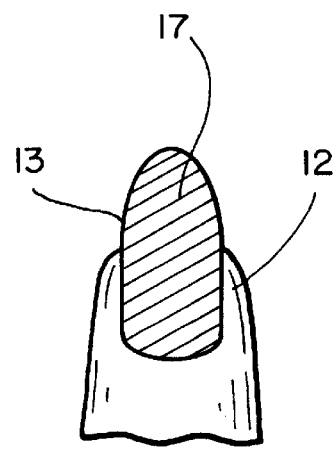
FIG_5

NAIL POLISHING METHOD AND PRODUCT

This invention pertains generally to nail care and treatment and, more particularly, to a method and product for polishing fingernails and the like.

Nail polishing generally consists of applying a film or coating of colored lacquer to the fingernails and/or toenails. The lacquer is most commonly applied with a small brush, although it is sometimes applied by other means such as an airbrush.

A significant problem in the application of nail polish is covering the entire nail without getting the polish on portions of the surrounding skin or tissue as well.

It is in general an object of the invention to provide a new and improved method and product for polishing fingernails and the like.

Another object of the invention is to provide a method and product of the above character which make it easy to cover the entire nail without leaving polish on the surrounding skin or tissue.

These and other objects are achieved in accordance with the invention by applying a masking material to the skin or tissue surrounding a nail, removing any portions of the masking material on the nail to form a sharp line of demarcation between the nail and the surrounding skin or tissue, applying a nail polishing lacquer to the nail and to portions of the masking material adjacent to the nail, allowing the lacquer to dry, and rubbing or wiping the masking material with a solvent to dissolve the material and thereby remove that material and any lacquer on it from the skin or tissue around the nail. In one disclosed embodiment, the masking material comprises a mixture of liquid detergent, calcium carbonate (chalk), toothpaste, water and a coloring agent and water.

FIGS. 1–3 are plan views illustrating certain steps in one embodiment of a nail polishing method incorporating the invention.

FIG. 4 is an isometric view illustrating another step in the process.

FIG. 5 is a plan view of a fingernail which has been polished in accordance with the invention.

In the embodiment illustrated, a masking material 11 is applied to the skin or tissue 12 surrounding a fingernail 13. The material has a paste-like consistency and is illustrated as being applied with a small brush 14. It can, however, be applied by any other suitable means, and it could even be applied by dipping the nail into the material.

The masking material is allowed to dry, and any of the material which happens to be on the nail itself is removed. In the embodiment illustrated, the material is scraped or pushed off the nail with an orange stick 16, but it can be removed with any other suitable implement, including another fingernail. The object is to leave the masking material on the skin but not the nail, with a sharp line of demarcation between the nail and the skin.

After the unwanted masking material has been removed from the nail and the remainder of the material has dried, a nail polishing lacquer 17 is applied to the nail. In the drawings, it is illustrated as being applied with a brush 18, but it can be applied by any other suitable means such as spraying. The lacquer is applied so that it covers the entire nail and overlaps onto the masking material on the skin or tissue surrounding the nail. The lacquer can be applied rapidly since it is not necessary to try to maintain a clean line between the nail and the skin.

The lacquer is preferably applied relatively thinly and with quick light strokes of the brush. This tends to produce a more even application and faster drying than a thicker coating with slow brush strokes.

Once the lacquer has dried, a solvent 19 is rubbed onto the masking material to dissolve it and thereby remove the material and any lacquer on it from the skin surrounding the nail. The lacquer breaks away cleanly along the edges of the nail, leaving the lacquer on the nail with a sharp line of demarcation between the nail and the surrounding skin or tissue. Suitable solvents include water and other solvents in which the masking material, but not the lacquer, is soluble. The solvent can be applied by any suitable means such as soaking and/or wiping, and in the embodiment illustrated, it is applied by dipping the fingers 21 into the solvent, then wiping it away with a towel. The material can also be removed quite effectively (almost instantly) by rubbing the solvent onto the material with a towel which has been moistened only slightly with the solvent.

Somewhat surprisingly, it has been found that the lacquer used for polishing nails is slightly permeable to water, although it is not attacked by the water and is often used as a barrier or sealant to water. Because the lacquer is bound to the mask but does not penetrate into the masking material even when the mask is very thin, the lacquer can easily be rubbed off, taking some or all of the mask with it. The process is aided by the presence of the solvent which removes the remainder of the masking material, i.e. any material which is not covered by lacquer or which is left behind when the lacquer is removed.

The masking material must go on wet but then dry quickly so as not to delay the application of the lacquer and to avoid being transferred onto clothes and the like. It should also adhere to the skin well enough to avoid being smudged or removed inadvertently. At the same time, however, the material should not be absorbed into the skin, or it will not come off as easily as it should.

One presently preferred masking material comprises a mixture of a coloring agent such as chalk, a liquid dishwashing detergent, toothpaste and water in the following proportions (by volume):

1 part colored chalk (calcium carbonate)
1 part liquid detergent
1 part toothpaste
1.4 parts water This formulation was developed empirically to provide a mixture which has a high solubility in water, goes on smoothly, dries quickly, does not separate, and does not bubble. In addition, it is non-toxic and will not harm the skin or tissue to which it is applied.

The chalk thickens the liquid detergent and serves as a water soluble colorizer which makes the mixture easier to see as it is applied to and removed from the nails. The detergent absorbs water quickly and cleanses the skin. The toothpaste contains glycerine and sodium lauryl sulfate which acts as a wetting agent and inhibits separation. The water controls the consistency of the mixture and aids in it rate of evaporation.

If desired, a soap can be used in addition to or in place of the detergent. However, soaps tend to cause bubbling and to absorb water more slowly than the detergent, and soaps also tend to stick to the skin more than detergents, making removal of the mask more than three times more difficult or time consuming. Soaps, therefore, are generally not as desirable as detergents for use in the mixture. It has also been found that some detergents work better than others in the mixture, with Palmolive Plus liquid dish washing detergent giving the best results. Other detergents such as Cheer laundry detergent do not work as well, nor do soaps such as Palmolive liquid dish washing soap and White King Laundry soap.

Similarly, another material such as sodium bicarbonate (baking soda) can be used in place of the toothpaste, although such materials are generally not as water absorbent, and they tend to separate from the mixture and create gaseous bubbles when shaken or exposed to heat. A preferred toothpaste is Colgate Winter Gel toothpaste. FMC microcrystalline cellulose can be used instead of toothpaste, but does not work as well.

For the coloring agent or chalk, Dixon Rail Road crayon chalk has been found to give good results, but Keson marking chalk has not.

Finally, alcohols can be used in place of some or all of the water to increase the rate of evaporation, but they have odors which may be unpleasant to some people.

Making the process work correctly requires a rather delicate balance of ingredients that stick together when dry or mostly dry, but do not stick to skin or nails. In addition, it is important that the lacquer not penetrate even thin films of the mask.

Initially, a product marketed by DuPont under the name "Liquid Glove" was tried as the masking material. That product contains a mixture of water, glycerin, sodium silicate and soap, and it tended to stick to the skin and nails, making removal much more difficult.

It is apparent from the foregoing that a new and improved nail polishing method and product have been provided. While only certain presently preferred embodiments have been described in detail, as will be apparent to those familiar with the art, certain changes and modifications can be made without departing from the scope of the invention as defined by the following claims.

I claim:

1. In a method of polishing nails, the steps of: applying a water soluble masking material comprising the ingredients of liquid detergent, toothpaste, a coloring agent and water to skin surrounding a nail and to portions of the nail, removing the masking material from the nail to form a sharp line of demarcation between the nail and the skin surrounding the nail, applying a nail polishing lacquer to the nail and to portions of the masking material adjacent to the nail, allowing the lacquer to dry, and removing the masking material and any lacquer on the masking material from the skin around the nail.

2. The method of claim 1 wherein the masking material is removed from the nail by pushing the material off the nail.

3. The method of claim 1 wherein the masking material is removed from the nail by pushing the material off the nail with an implement selected from the group consisting of an orange stick and a fingernail.

4. The method of claim 1 wherein the masking material is removed from the skin surrounding the nail by dissolving the masking material with water.

5. In a method of polishing nails, the steps of: applying a masking material comprising the ingredients of liquid detergent, toothpaste, a coloring agent and water to skin surrounding a nail and to portions of the nail, removing the masking material from the nail to form a sharp line of demarcation between the nail and the skin surrounding the nail, applying a nail polishing lacquer to the nail and to portions of the masking material adjacent to the nail, allowing the lacquer to dry, and applying a solvent to the masking material to dissolve the material and thereby remove that material and any lacquer on it from the skin around the nail.

6. The method of claim 5 wherein the solvent is applied by rubbing it onto the material.

7. In a method of polishing nails, the steps of: applying a water soluble masking material comprising a mixture of liquid detergent, toothpaste, a coloring agent and water to skin surrounding a nail, removing any portions of the masking material on the nail to form a sharp line of demarcation between the nail and the skin surrounding the nail, applying a nail polishing lacquer to the nail and to portions of the masking material adjacent to the nail, allowing the lacquer to dry, and dissolving the masking material with water to remove the masking material and any lacquer on the masking material from the skin around the nail.

8. The method of claim 5 wherein the masking material is removed from the nail by pushing the material off the nail.

9. The method of claim 5 wherein the masking material is removed from the nail by pushing the material off the nail with an implement selected from the group consisting of an orange stick and a fingernail.

10. The method of claim 5 wherein the masking material is removed from the skin surrounding the nail by rubbing the material with water.

11. The method of claim 4 wherein the water is rubbed onto the masking material.

12. The method of claim 1 wherein the masking material has a pasty consistency when it is applied.

13. The method of claim 5 wherein the masking material has a pasty consistency when it is applied.

* * * * *